United States Patent [19]

Axen et al.

[11] 4,321,370

[45] Mar. 23, 1982

[54] 2,5-INTER-O-PHENYLENE-3,4-DINOR-6,9α-EPOXY-6β-PGF₁ COMPOUNDS

[75] Inventors: Udo F. Axen, Plainwell; John C. Sih, Kalamazoo, both of Mich.

[73] Assignee: The Upjohn Company, Kalamazoo, Mich.

[21] Appl. No.: 165,837

[22] Filed: Jul. 3, 1980

Related U.S. Application Data

[60] Division of Ser. No. 62,443, Jul. 31, 1979, which is a continuation-in-part of Ser. No. 962,845, Nov. 22, 1978, abandoned.

[51] Int. Cl.³ .......................................... C07D 307/935
[52] U.S. Cl. .................................. 542/426; 542/429; 260/346.22; 260/346.73
[58] Field of Search ................... 260/346.22; 542/426, 542/429

[56] References Cited

U.S. PATENT DOCUMENTS 4,175,202  11/1979  Nelson ................................. 562/463

*Primary Examiner*—John M. Ford
*Assistant Examiner*—Bernard Dentz
*Attorney, Agent, or Firm*—Robert A. Armitage

[57] ABSTRACT

The present invention provides 2,5-inter-o-phenylene-3,4-dinor-6,9α-epoxy-6β-PGF₁ compounds. These compounds are useful for a wide variety of pharmacological and therapeutical purposes, e.g., as antithrombotic agents.

1 Claim, No Drawings

2,5-INTER-O-PHENYLENE-3,4-DINOR-6,9α-EPOXY-6β-PGF$_1$ COMPOUNDS

DESCRIPTION

Cross Reference to Related Application

This application is a division of Ser. No. 62,443, filed 31 July 1979, now pending, which is a continuation-in-part of Ser. No. 962,845, filed 22 Nov. 1978, now abandoned.

BACKGROUND OF THE INVENTION

The present invention relates to novel prostacyclin analogs and intermediates for their production. Most particularly, the present invention provides 2,5-inter-o-phenylene-3,4-dinor-6,9α-epoxy-6β-PGF$_1$ compounds. The preparation and use of the novel compounds described herein is incorporated here by reference from U.S. Pat. No. 4,281,113.

SUMMARY OF THE INVENTION

The present invention particularly provides a prostacyclin analog of formula VI

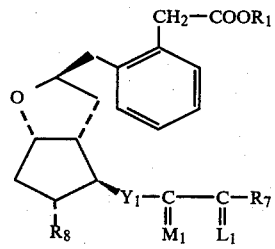

wherein
R$_8$ is hydrogen, hydroxy, or hydroxymethyl;
wherein
Y$_1$ is
 (1) trans—CH=CH—,
 (2) cis—CH=CH—,
 (3) —CH$_2$CH$_2$, or
 (4) —C≡C—,
wherein M$_1$ is α—R$_5$:β—OH or α—OH:β—R$_5$, wherein R$_5$ is hydrogen or alkyl with one to 4 carbon atoms, inclusive,
wherein L$_1$ is α—R$_3$:β—R$_4$, α—R$_4$:β—R$_3$, or a mixture of α—R$_3$:β—R$_4$ and a—R$_4$:β—R$_3$, wherein R$_3$ and R$_4$ are hydrogen, methyl, or fluoro, being the same or different, with the proviso that one of R$_3$ and R$_4$ is fluoro only when the other is hydrogen or fluoro;
wherein R$_7$ is
 (1) —(CH$_2$)$_m$—CH$_3$, wherein m is an integer from one to 5, inclusive;
 (2) phenoxy;
 (3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
 (4) phenyl;
 (5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
 (6) phenylmethyl, phenylethyl, or phenylpropyl; or
 (7) phenylmethyl, phenylethyl, or phenylpropyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
with the proviso that R$_7$ is phenoxy or substituted phenoxy, only when R$_3$ and R$_4$ are hydrogen or methyl, being the same or different;
wherein
R$_1$ is
 (1) hydrogen;
 (2) alkyl of one to 12 carbon atoms, inclusive;
 (3) cycloalkyl of 3 to 10 carbon atoms, inclusive;
 (4) aralkyl of 7 to 12 carbon atoms, inclusive;
 (5) phenyl;
 (6) phenyl substituted with one, 2 or 3 chloro or alkyl of one to 3 carbon atoms;
 (7) phenyl substituted in the para position by
  (a) —NH—CO—R$_{25}$,
  (b) —CO—R$_{26}$,
  (c) —O—CO—R$_{27}$, or
  (d) —CH=N—NH—CO—NH$_2$
wherein
R$_{25}$ is methyl, phenyl, acetamidophenyl, benzamidophenyl, or —NH$_2$; R$_{26}$ is hydroxy, methyl, phenyl, —NH$_2$, or methoxy; and R$_{27}$ is phenyl or acetamidophenyl, inclusive; or a pharmacologically acceptable salt thereof when R$_1$ is hydrogen.

The novel prostaglandin analogs are useful for a variety of prostacyclin-like pharmacological purposes, particularly and especially as inhibitors of platelet aggregation in vivo and in vitro. Thus, these prostacyclin analogs are useful for a variety of pharmacological and therapeutical purposes, e.g., as antithrombotic agents.

We claim:
1. A prostacyclin analog of formula VI

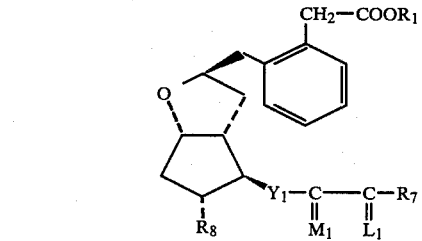

wherein
R$_8$ is hydrogen, hydroxy, or hydroxymethyl;
wherein
Y$_1$ is
 (1) trans—CH=CH—,
 (2) cis—CH=CH—,
 (3) —CH$_2$CH$_2$, or
 (4) —C≡C—,
wherein
M$_1$ is α—R$_5$:β—OH or α—OH:β—R$_5$, wherein R$_5$ is hydrogen or alkyl with one to 4 carbon atoms, inclusive,
wherein
L$_1$ is α—R$_3$:β—R$_4$, α—R$_4$:β—R$_3$, or a mixture of α—R$_3$:β—R$_4$ and α—R$_4$:β—R$_3$, wherein R$_3$ and R$_4$ are hydrogen, methyl, or fluoro, being the same or different, with the proviso that one of R$_3$ and R$_4$ is fluoro only when the other is hydrogen or fluoro;
wherein $R_7$ is (1) —$(CH_2)_m$—$CH_3$, wherein m is an integer from one to 5, inclusive;
(2) phenoxy;
(3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;

wherein
  $R_1$ is
  (1) hydrogen;
  (2) alkyl of one to 12 carbon atoms, inclusive;
  (3) cycloalkyl of 3 to 10 carbon atoms, inclusive;
  (4) aralkyl of 7 to 12 carbon atoms, inclusive;
  (5) phenyl;
  (6) phenyl substituted with one, 2 or 3 chloro or alkyl of one to 3 carbon atoms;
  (7) phenyl substituted in the para position by
    (a) —NH—CO—$R_{25}$,
    (b) —CO—$R_{26}$,
    (c) —O—CO—$R_{27}$, or
    (d) —CH=N—NH—CO—$NH_2$
wherein $R_{25}$ is methyl, phenyl, acetamidophenyl, benzamidophenyl, or —$NH_2$; $R_{26}$ is hydroxy, methyl, phenyl, —$NH_2$, or methoxy; and $R_{27}$ is phenyl or acetamidophenyl, inclusive, or a pharmacologically acceptable salt thereof when $R_1$ is hydrogen.

* * * * *